United States Patent [19]
Milanese

[11] Patent Number: 5,808,058
[45] Date of Patent: Sep. 15, 1998

[54] PROCESS FOR THE PREPARATION OF 10-OXO-10, 11-DIHYDRO-5H-DIBENZ (B,F) AZEPIN-5-CARBOXAMIDE

[75] Inventor: Alberto Milanese, Milan, Italy

[73] Assignee: Trifarma S.r.l., Milan, Italy

[21] Appl. No.: 765,481

[22] PCT Filed: Jan. 3, 1996

[86] PCT No.: PCT/EP96/00004

§ 371 Date: Dec. 24, 1996

§ 102(e) Date: Dec. 24, 1996

[87] PCT Pub. No.: WO96/21649

PCT Pub. Date: Jul. 18, 1996

[30] Foreign Application Priority Data

Jan. 13, 1995 [IT] Italy ............................. MI95 A 0056

[51] Int. Cl.⁶ ................................................. C07D 223/18
[52] U.S. Cl. ............................................................ 540/588
[58] Field of Search ............................................. 540/588

[56] References Cited

FOREIGN PATENT DOCUMENTS 2011087  9/1970  Germany .
4307181  10/1994  Germany .

OTHER PUBLICATIONS

Ahmad et al, Heterocycles, vol. 24, No. 12, 1986.

*Primary Examiner*—Yogendra N. Gupta
*Attorney, Agent, or Firm*—Bucknam and Archer

[57] ABSTRACT

A novel process for the preparation of 10-oxo-10,11-dihydro-5H-dibenz(b,f)azepin-5-carboxamide (VI) consists of starting group 10-methoxy-5H-dibenz(b,f)azepine (IV) and subjecting compound (IV) to direct carbamoylation with isocyanic acid generated in situ from cyanates and acids and then subjecting the product to acid hydrolysis of the enol ether. An alternative process to obtain (VI) starts (IV) effecting the hydrolysis reaction before the carbamoylation. In this case the carbamoylating agent is chlorosulfonyl isocyanate.

9 Claims, No Drawings

PROCESS FOR THE PREPARATION OF 10-OXO-10, 11-DIHYDRO-5H-DIBENZ (B,F) AZEPIN-5-CARBOXAMIDE

SUMMARY OF THE INVENTION

The present invention relates to a process for the preparation of 10-oxo-10,11-dihydro-5H-dibenz(b,f)aze-pin-5-carboxamide (IV), also known under the non-proprietary name of oxcarbazepine, a substitute for carbamazepine, starting from 10-methoxy-5H-dibenz(b,f)azepine IV by means of direct carbamoylation with isocyanic acid generated in situ from cyanates and acids and subsequent acid hydrolysis of the enol ether, according to scheme A:

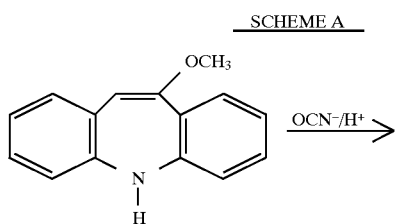

Alternatively, according to a further object of the invention, the hydrolysis reaction can be carried out before the carbamoylation, according to scheme B:

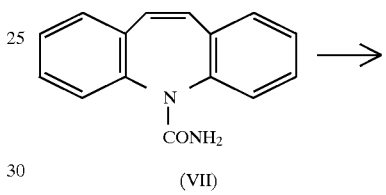

The chemical synthesis of oxcarbazepine is not immediate, in fact a number of alternative routes, very different from each other, are known at present. The main ones are summarized in the following schemes.

SCHEME C

Oxidation of the carbamazepine VII to 10,11-oxiran derivative VIII and rearrangement of the latter to oxcarbazepine VI (German Patent 2,246,842 and Swiss Patent 633,271)

The main drawbacks of this process resides in the use, as a reagent, of the carbamazepine which is expensive, being itself a final product; moreover, the epoxidation reaction gives poor yields, due to the substrate sensitivity, when using conventional epoxidizers such as peracetic acid, or it requires remarkable excesses of expensive reagents such as 3-chloroperbenzoic acid. Moreover, dangerous side-products form during the epoxidation process. The rearrangement reaction epoxide - - - > ketone takes place with important amounts of expensive catalysts, is delicate since a variety of side-products are formed, and it yields a crude product which requires thorough purifications giving low yields.

SCHEME D

Nitration of 5-cyano-5H-dibenz(b,f)azepine (IX, N-cyanoiminostilbene) at the position 10 (X), followed by reduction of the nitro group to amino group and simultaneous hydrolysis of the enamine to ketone, to obtain 10-oxo-10,11-dihydro-5-cyano-5H-dibenz(b,f)azepine (IX) which is hydrolyzed to oxcarbazepine VI (EP-A-0 028 028).

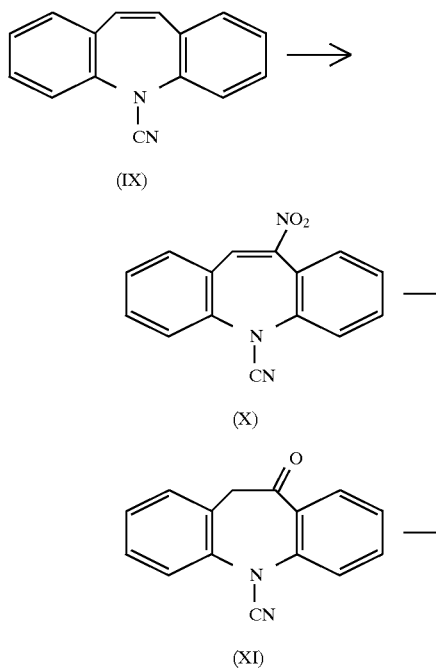

The drawbacks of this process consist above all in the starting product IX which can be obtained, according to EP-A-0029409, either from carbamazepine VII which is an expensive product, or from 5H-dibenz-(b,f)azepine (iminostilbene I) by reaction with cyanogen chloride, which is a toxic gas difficult to handle:

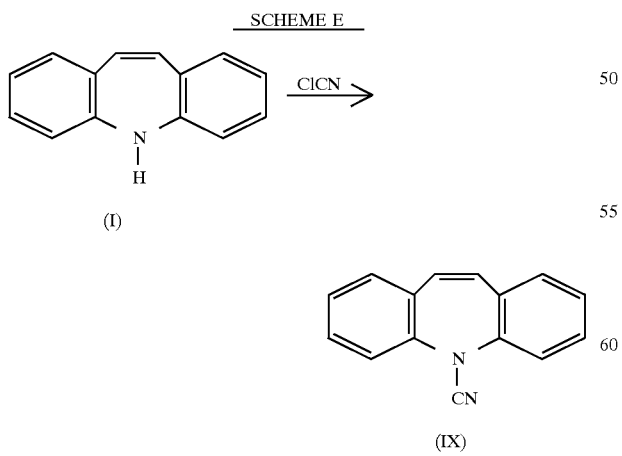

Moreover, the nitration gives acceptable yields only if carried out with nitrating agents such as $N_2O_3$ or $N_2O_4$, which are difficult to use. Finally the hydrolysis of the cyano group requires preferably the use of $BF_3$ complexes, which are expensive and must be handled carefully since they are very aggressive. The total yield of the process is low.

SCHEME F

Hydrolysis of the 10 chloro-5H-dibenz(b,f)azepin carboxamide with concentrated sulfuric acid, to give directly oxcarbazepine (Swiss Patent 642,950).

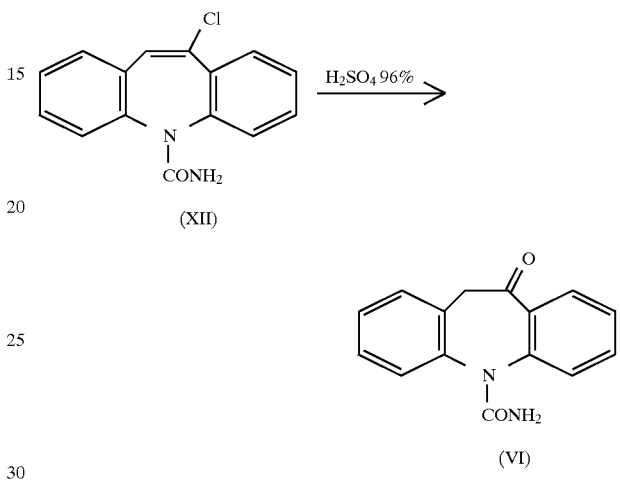

Actually, the hydrolysis reaction is very slow and essentially incomplete at the indicated temperature, whereas an even slight raising of the temperature yields a degradation.

Moreover the preparation of XII requires either the reaction of phosgene, a toxic gas, with 10-chloro-5H-dibenz(b,f)azepine (XIII) or the carbamazepine VII according to the Scheme G and G' as the starting reagent:

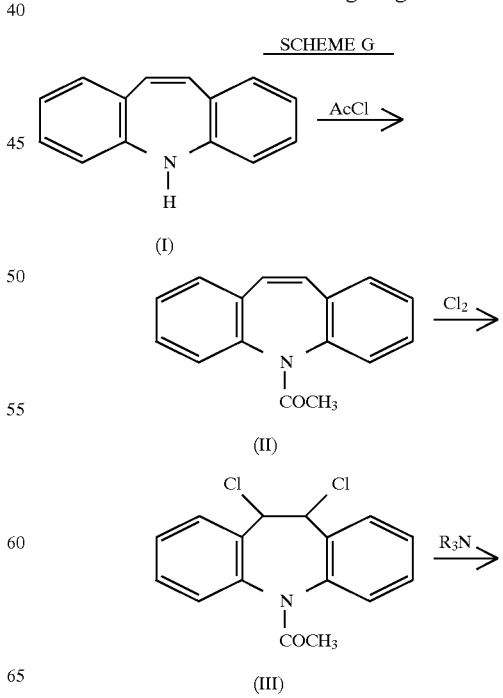

-continued
SCHEME G

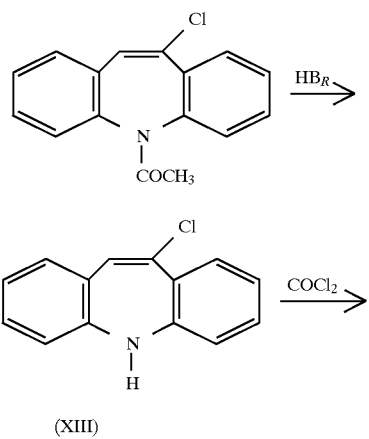

(XIII)

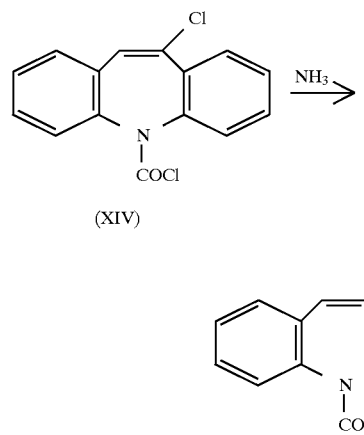

(XIV)

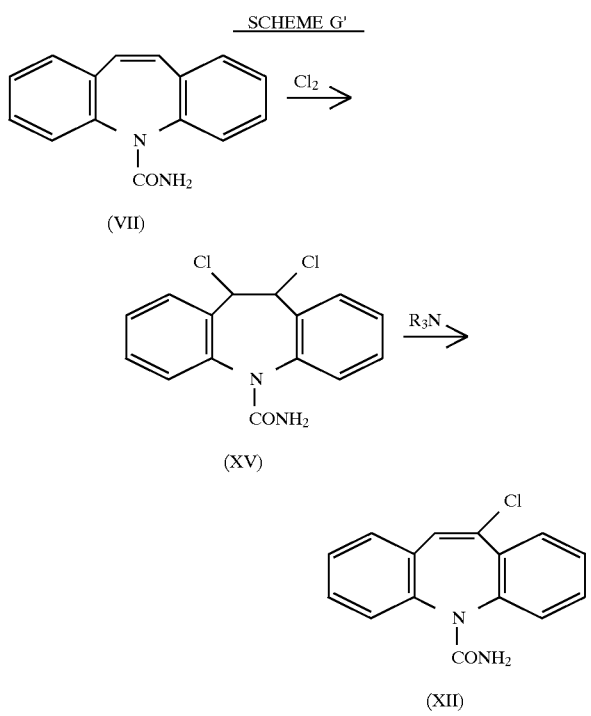

SCHEME G'

(VII)

(XV)

(XII)

Whereas scheme G involves a great number of steps, the drawback of scheme G' resides in the high cost of the starting material VII.

SCHEME H

Carbamoylation reaction of 10-methoxyminostilbene IV by treatment with phosgene followed by ammonolysis of the chlorocarbonyl derivative XVI and hydrolysis of the vinyl ether V (German Patent 2,011,087)

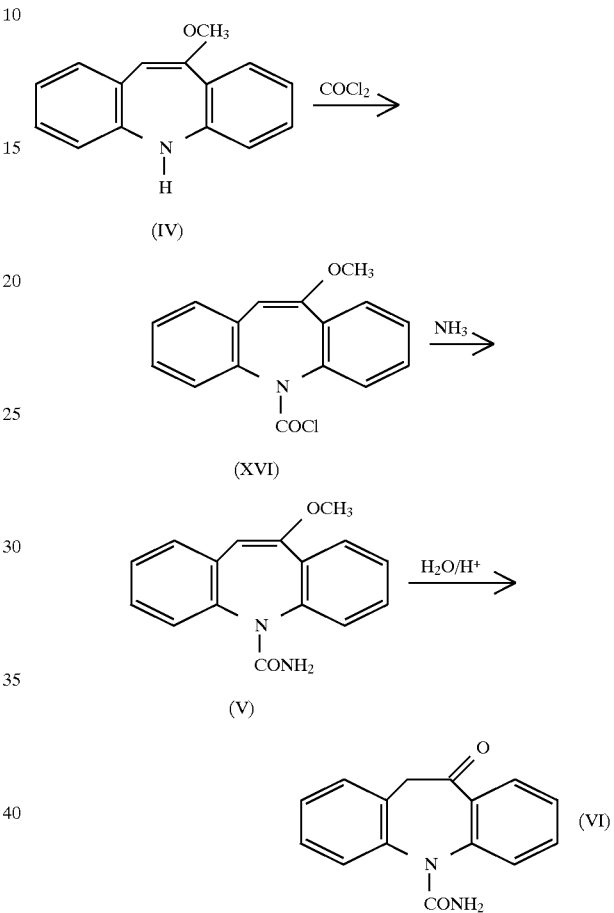

(IV)

(XVI)

(V)

(VI)

The most important problem with this process is the use of phosgene, a toxic gas which is subjected to very severe regulations.

Now it has surprisingly been found that the carbamoylation reaction of 10-methoxyminostilbene IV takes place in very good yields and in a single step from IV to V (scheme A), by means of isocyanic acid generated in situ from metal cyanates and acids. Moreover the carbamoyl derivative V can be hydrolyzed with aqueous mineral acids, without isolation, directly in the reaction environment to give a crude oxcarbazepine which, upon a single crystallization, yields a product of excellent purity. This is even more surprising since this type of carbamoylation does not occur on all kind of substrates; in fact it was tried first on 10-ketoiminodibenzyl V bis, obtained by hydrolysis from the enol ether IV, with no results, not even traces. Subsequently V bis was found to be barely reactive in these conditions, in fact it reacts only with chlorosulfonyl isocyanate, the most reactive of the known isocyanates (scheme B).

The process is remarkably interesting due to the easiness of availability and handling of the reagents used as well as since 10-methoxyiminostilbene IV can be obtained in nearly quantitative yields starting from iminostilbene I, according to the process shown in scheme K.

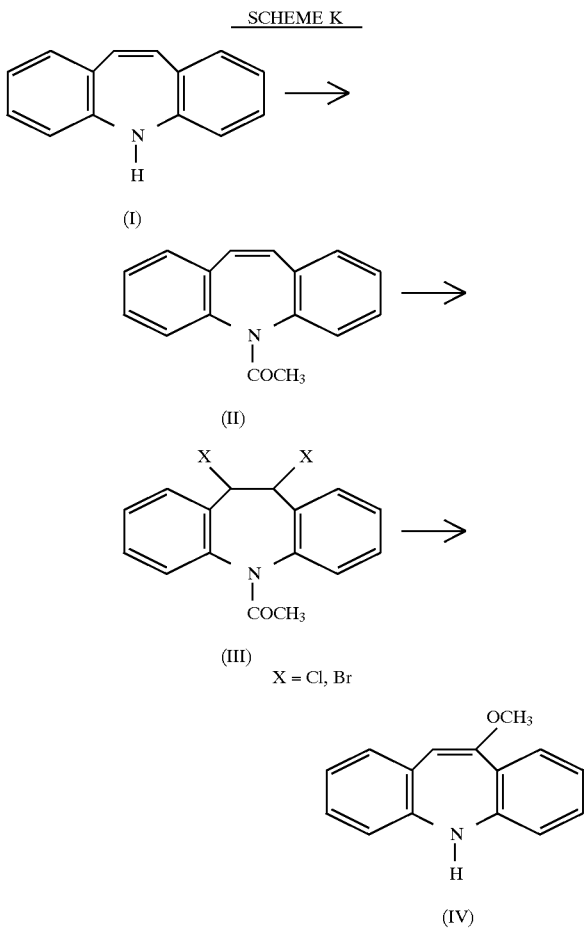

SCHEME K

X = Cl, Br

This process is disclosed in Belgian Patent 597,793 and in U.S. Pat. No. 27,622. Contrary to what stated in EP-A-0 028 028, the process is simple and easily reproducible and, when correctly applied, it gives excellent yields.

According to the invention, 10-methoxyiminostilbene IV is reacted with an alkali or alkaline-earth (preferably sodium or potassium) cyanate, in an equimolar amount or in a slight excess, in an aprotic organic solvent such as an aromatic hydrocarbon, or in a chlorinated solvent such as toluene, benzene, chlorobenzene, dichloromethane, chloroform, 1,2-dichloroethane, 1,1,1-trichloroethane, trichloroethylene, at temperatures from 20° to 60° C.

A mineral acid such as 98% sulfuric acid 98%, anhydrous hydrochloric or hydrobromic acids or the solutions thereof in acetic acid, or acetic, formic, monochloroacetic, monobromoacetic, dichloroacetic, trichioroacetic, propionic, 2-chloropropionic acids are added to the mixture, in an amount equimolar to the cyanate. Catalytic amounts of water or alcohols can increase the reaction rate.

The mixture is stirred quickly for some hours, until completion of the carbamoylation reaction, diluted with water, the phases are separated and the organic phase is concentrated; the residue is hydrolyzed with a diluted mineral acid, such as hydrochloric, hydrobromic or sulfuric acid, under reflux. The crude solid product is pump-filtered or centrifuged, washed and recrystallized from solvents such as acetone, methanol, dioxane, dimethylformamide, dimethylacetamide, cycloexanone, methylcellosolve, ethylcellosolve, butylcellosolve, also in mixture with water.

Alternatively, 10-oxo-10,11-dihydro-5H-dibenz(b,f)azepin-5-carboxamide VI can be obtained starting from 10-methoxy-5H-dibenz(b,f)azepine according to the scheme B.

The enol ether group of compound IV is hydrolyzed to ketone with diluted mineral acids such as hydrochloric, hydrobromic or 10% sulfuric acid. The 10-oxo-10,11-dihydro-5H-dibenz(b,f)azepine V bis is then carbamoylated with chlorosulfonyl isocyanate in anhydrous chlorinated solvents such as chloroform or dichloromethane or other.

After hydrolyzing the chlorosulfonyl group with water and ice and recrystallizing from one of the solvents mentioned above for scheme A, product VI in a good purity degree is obtained.

The invention is further illustrated in the following examples.

EXAMPLE 1

10-oxo-10,11-dihydro-5H-dibenz(b,f)azepin-5-carboxamide 22.3 g (0.1 moles) of 10-methoxy-5H-dibenz(b,f)azepine prepared according to U.S. Pat. No. 27,622 are dissolved in 150 ml of toluene. 8.92 g (0.11 moles) of potassium cyanate and 10.8 g (0.11 moles) of 96% sulfuric acid are added. The mixture is heated between 40° and 50° C. stirring vigorously for 24 hours. When the analytical control detects a starting product content<2%, 50 ml of water are dropped into the mixture, which is stirred and the phases are separated. The organic phase is evaporated to dryness under vacuum and taken up into 100 ml of 10% sulfuric acid. The mixture is refluxed for 2–3 hours, cooled at room temperature and pump-filtered, washing with water; then it is recrystallized from dimethylacetamide (50 ml), filtered through charcoal washing the precipitate on the filter with acetone, and dried under vacuum. The product is identified by IR, NMR and mass spectroscopies.

Yield g 15.5 m.p. 222° C.

EXAMPLE 2

The procedure of example 1 is repeated, using equimolar amounts of trichloroacetic acid instead of sulfuric acid; the reaction lasts 48 hours. The product is recrystallized from cyclohexanone.

Yield g 14.3 m.p. 222° C.

EXAMPLE 3

The procedure of example 2 is repeated, using dichloromethane under reflux instead of toluene.

Yield g 14.8 m.p. 221° C.

EXAMPLE 4

The procedure of example 1 is repeated, replacing sulfuric acid with an equimolar amount of anhydrous hydrochloric acid dissolved in acetic acid and using chloroform as the solvent.

Yield g 16.2 m.p. 222° C.

EXAMPLE 5

The procedure of example 2 is repeated, using chloroform as the solvent and recrystallizing from ethylcellosolve.

Yield g 15 m.p. 222° C.

EXAMPLE 6

The procedure of example 1 is repeated, using an equimolar amount of sodium cyanate instead of potassium cyanate.

Yield g 16.5 m.p. 221° C.

EXAMPLE 7

The procedure of example 6 is repeated, using equimolar amounts of monochloroacetic acid instead of sulfuric acid, and hydrolyzing with 2N hydrochloric acid.

Yield g 11.5 m.p. 223° C.

EXAMPLE 8

The procedure of example 7 is repeated, using chloroform and recrystallizing from ethylcellosolve.

Yield g 12.7 m.p. 222° C.

EXAMPLE 9

The procedure of example 6 is repeated, using equimolar amounts of trichloroacetic acid instead of sulfuric acid, chloroform as the solvent and adding 0.5 ml of water. The reaction lasts 4 hours. The product is recrystallized from dimethylformamide and water 2÷1.

Yield g 13.5 m.p. 223° C.

EXAMPLE 10

The procedure of example 9 is repeated, using dichloroacetic acid in equivalent amount and recrystallizing from methanol.

Yield g 14.8 m.p. 224° C.

EXAMPLE 11

10-oxo-10,11-dihydro-5H-dibenz(b,f)azepine 22.3 g of 10-methoxy-5H-dibenz(b,f)azepine are heated under reflux with 100 ml of 2N hydrochloric acid for 2 hours. The gummy residue is extracted with chloroform (50÷50 ml), the combined extracts are washed with water and evaporated to dryness under vacuum. The residue is taken up into 200 ml of ethanol, treated with charcoal (2 g) for 1 h under reflux, filtered, evaporated to dryness under vacuum, finally taken up into 50÷50 ml of toluene, stripping thoroughly. The residue is kept for further working-up.

Yield g 20

EXAMPLE 12

10-oxo-10,11-dihydro-5H-dibenz(b,f)azepin-5-carboxamide

The product from example 11 is taken up into 200 ml of chloroform and in this solution, always maintained below 25° C., 15.8 g of chlorosulfonyl isocyanate (0.11 moles) dissolved in 50 ml of chloroform are dropped therein, shielding from room humidity. The mixture is stirred at room temperature overnight and triturated ice (200 g) is poured therein, stirring thoroughly for a further 24 hours. The phases are separated, the aqueous phase is extracted with chloroform (20÷20 ml) and the combined extracts are evaporated to dryness under vacuum. The residue is taken up into hot acetone, obtaining a crude product which is recrystallized from dioxane, to yield 8.5 of a good quality product.

m.p. 220°–222° C.

I claim:

1. A process for the preparation of 10-oxo-10,11-dihydro-5H-dibenz(b,f)azepin-5-carboxamide of formula (VI)

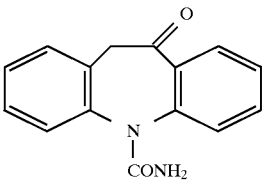

which comprises the steps of:
a) reacting 10-methoxy-5H-dibenz(b,f)azepine of formula (IV)

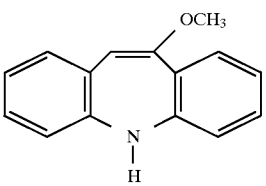

with an alkali or alkaline-earth cyanate, in the presence of an acid selected from the group consisting of 98% sulfuric acid, anhydrous hydrochloric acid, anhydrous hydrobromic acid, glacial acetic acid, formic acid, monochloroacetic acid, monobromoacetic acid, dichloroacetic acid, trichloroacetic acid, propionic acid and 2-chloropropionic acid, and said acid is used in equimolar amount or in slight excess whereby the product 10-methoxy 5-dibenz-azepine of formula (V)

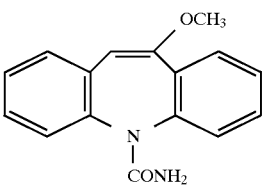

is obtained and then
b) hydrolyzing with an acid said compound (V) to obtain crude compound (VI) and
c) purifying said crude compound (VI) by recrystallization.

2. The process according to claim 1 wherein step a) is carried out in an aromatic solvent or a chlorinated hydrocarbon or a mixture thereof.

3. The process according to claim 2 wherein said solvent is a member selected from the group consisting of benzene, toluene, chlorobenzene, dichloromethane, chloroform, 1,2-dichloroethane, 1,1,1-trichloroethane and trichloroethylene.

4. The process according to claim 3 wherein said step a) is carried out in the presence of a catalytic amount of water or an alcohol.

5. The process according to claim 1 wherein said step b) is carried out with a dilute mineral acid.

6. The process according to claim 5 wherein said acid is hydrochloric, hydrobromic or 10% sulfuric acid.

7. The process according to claim 1 wherein said step c) is carried out in a solvent which is a member selected from the group consisting of acetone, methanol, dioxane, dimethylformamide, dimethylacetamide, cyclohexanone, methylcellosolve and mixtures thereof with water.

8. The process according to claim 1 wherein the reaction mixture from step a) which contains said compound (V) is hydrolyzed in step b).

9. The process according to claim 1 wherein said 98% sulfuric acid, said anhydrous hydrochloric acid and said anhydrous hydrobromic acid are in solution in acetic acid.

* * * * *